United States Patent [19]

Thorn et al.

[11] Patent Number: 5,258,469
[45] Date of Patent: Nov. 2, 1993

[54] PREPARATION OF 2-(PYRIDYL)ETHYL BIS-(TRIALKYL SILYL)PHOSPHONATE DERIVATIVES SUBSTITUTED PHOSPHOROUS COMPOUNDS

[75] Inventors: David L. Thorn, West Chester, Pa.; Owen W. Webster; Robert C. Wheland, both of Wilmington, Del.

[73] Assignee: E. I. Du Pont de Nemours and Company, Wilmington, Del.

[21] Appl. No.: 957,151

[22] Filed: Oct. 7, 1992

Related U.S. Application Data

[62] Division of Ser. No. 649,542, Jan. 24, 1991, Pat. No. 5,194,616.

[51] Int. Cl.$^5$ .............................................. C08G 69/48
[52] U.S. Cl. .................................. 525/420; 525/419; 546/14
[58] Field of Search ................ 525/420, 419; 528/354; 546/14

[56] References Cited

U.S. PATENT DOCUMENTS

| | | | |
|---|---|---|---|
| 4,299,943 | 12/1981 | Digiacomo et al. | 528/9 |
| 4,788,254 | 1/1988 | Kawakubo et al. | 525/100 |
| 4,912,175 | 3/1990 | Wheland et al. | 525/420 |

FOREIGN PATENT DOCUMENTS 0353969  2/1990  European Pat. Off.

OTHER PUBLICATIONS

E. Maruszewska-Wieczorkwska & J. Michalski, J. Org. Chem., vol. 23, pp. 1886–1889 (1958).
E. Boyd, et al., Tet. Lett., vol. 31, pp. 2933–2936 (1990).
J. K. Thottabil, et al., Tet. Lett., vol. 25, pp. 4741–4744 (1984).
M-P. Teulade & P. Savignac Synthesis-Stutt., vol. 11, pp. 1037–1039 (1987).
Hersman et al., "Nitrogen Compounds of the Phosphoric and Phosphoric Acids IV. Some Derivatives of Phenylphomamidic and phenylphosphonamidothioic. Acids", Jul. 11, 1958.

*Primary Examiner*—Morton Foelak
*Assistant Examiner*—Shelley A. Dodson
*Attorney, Agent, or Firm*—Susan B. Evans

[57] ABSTRACT

A process for producing phosphonate esters containing the 2-(pyridyl)ethyl group by reacting a vinylpyridine with a di- or trihydrocarbylphosphite in the presence of a selected silane, protic acid, or Lewis acid is disclosed. Also disclosed are novel silylphosphonate esters containing the 2-(pyridyl)ethyl group. All of the compounds produced herein are useful as catalysts for increasing the molecular weight of polyamides.

7 Claims, No Drawings

PREPARATION OF 2-(PYRIDYL)ETHYL BIS-(TRIALKYL SILYL)PHOSPHONATE DERIVATIVES SUBSTITUTED PHOSPHOROUS COMPOUNDS

This is a division of application Ser. No. 07/649,542, filed Jan. 24, 1991, now U.S. Pat. No. 5,194,616.

FIELD OF INVENTION

A process for the preparation of 2-(pyridyl)ethyl substituted phosphorous compounds, by contacting a vinylpyridine and a phosphorous compound in the presence of a silicon halide, a protic acid, or a selected Lewis acid. Also provided are novel 2-(pyridyl)ethyl (bis)silylphosphonates and their use as catalysts in increasing the molecular weight of polyamides.

BACKGROUND OF THE INVENTION

The reaction of dihydrocarbylphosphites with a variety of olefinic unsaturated organic compounds, so that a phosphorous-carbon bond is formed, is known in the art, see for background for example: X. Lu and J. Zhu, Synthesis, p. 563-564 (1986); G. Optiz, et. al., Ann., vol. 665, p. 91-101 (1963); I. Tyurenkov, et. al., Khim. Farm. Zh., vol. 22, p. 170-174 (1988); V. Shchepin, et. al., Zh. Obshch. Khim., vol. 57, p. 2144 (1987); and V. Ovchinnikov, et. al., Zh. Obshch. Khim., vol. 54, p. 1916-1917 (1984). None of these disclose the use of vinylpyridines in such reactions.

E. Maruszewska-Wieczorkowska and J. Michalski, J. Org. Chem., vol. 23, p. 1886-1889 (1958) report the synthesis of various 2-(pyridyl)phosphonates by the reaction of a vinylpyridine with a dialkyl phosphite, optionally with a sodium ethoxide catalyst. Without the catalyst, it was reported that yields were lower, and considerable amounts of polymeric substances were formed. Sodium ethoxide, the catalyst used by these authors, is a base, and no mention is made of the use of halogen containing or acidic catalysts, as used herein.

E. Boyd, et. al., Tet. Lett., vol. 31, p. 2933-2936 (1990), report the reaction of triethylammonium phosphinate, trimethylchlorosilane, and alpha,beta-unsaturated ester (such as an acrylate) resulted in the formation of (beta-ester)alkyl substituted phosphonic acid. Bis(trimethylsilyl)phosphinite was postulated as an intermediate. However, only alpha-beta unsaturated esters are reported to be suitable reactants.

Similarly, J. K. Thottahil, et. al., Tet. Lett., vol. 25, p. 4741-4744 (1984), reports that phosphonous esters in the presence of trimethylchlorosilane, and triethylamine react with substrates suitable for Michael addition type reactions (i.e., alpha, beta unsaturated esters and aldehydes) to give various addition products to the phosphonous ester. Depending on the reactants, 1,2 or 1,4 addition was obtained. N,O-Bis(trimethylsilyl)acetamide could be used in place of trimethylchlorosilane. No mention is made in this paper of using amines, such as a vinylpyridine, as substrates.

M-P. Teulade and P. Savignac, Synthesis-Stutt., vol. 11, p. 1037-1039 (1987) report the reaction of triethyl phosphite with alpha-beta unsaturated aldimines catalyzed by formic acid. No mention is made of using vinylpyridines as reactants.

U.S. Pat. No. 4,912,175 describes the use of 2-(pyridyl)ethyl phosphonic esters and acids as catalysts for increasing the molecular weight of polyamides such as nylon 6,6. No mention is made of the use of silyl esters as such catalysts.

It is the object of this invention to provide a convenient, high yield and economic synthesis of 2-(pyridyl)ethyl substituted phosphonate esters, which are useful catalysts for increasing the molecular weight of polyamides. Another objective is to provide novel 2-(pyridyl)ethyl substituted bis(silyl)phosphonate esters that are also useful as catalysts for increasing the molecular weight of polyamides.

SUMMARY OF THE INVENTION

This invention concerns a process for the production of 2-(pyridyl)ethyl substituted phosphorous compounds, comprising, contacting (1) a first compound selected from the group consisting of $P(OR^1)_3$ and $HP(O)(OR^1)_2$, wherein each $R^1$ is independently alkyl, substituted alkyl, silyl, or substituted silyl with (2) a vinylpyridine, and (3) a third compound selected from the group consisting of (a) a silane of the formula $R^2{}_nSiX_{4-n}$ wherein each $R^2$ is independently hydrocarbyl or substituted hydrocarbyl, each X is independently chlorine, bromine, or an oxyanion whose conjugate acid has a pKa, when measured in water, of less than about 2, and n is 0, 1, 2, or 3;

(b) a protic acid of the formula HPY wherein Y is an anion and p is the valence of Y, provided said protic acid has a pKa of about 6 or less in water; and (c) a Lewis acid of the formula $MZ_q$, wherein M is a metal or metalloid atom, Z is hydrocarbyl, chlorine or bromine, and q is the valence of M;

and provided that when said third compound is (a) or (c) said first compound is $HP(O)(OR^1)_2$, and further provided that when said third compound is (b) said first compound is $P(OR^1)_3$.

This invention also concerns a compound of the formula

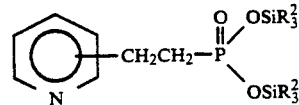

wherein each $R^3$ is independently hydrocarbyl or substituted hydrocarbyl.

This invention also concerns a process for increasing the molecular weight of a polyamide comprising heating a polyamide in the presence of a compound of the formula

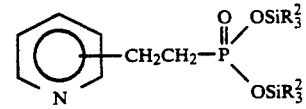

wherein each $R^2$ is independently hydrocarbyl or substituted hydrocarbyl.

DETAILED DESCRIPTION OF THE INVENTION

This invention concerns a method of producing 2-(pyridyl)ethyl substituted phosphorous compounds of the general type

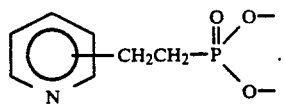

Specific compounds and their uses are also claimed. The 2-(pyridyl)ethyl group is derived (in synthesis) from a vinylpyridine of the structure

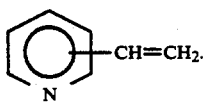

The ring carbon atoms of the pyridine ring may be substituted with groups that do not interfere with the reactions herein, such as alkyl and alkoxy. Preferred vinylpyridine compounds herein for all processes and compounds (and their corresponding groups when bound to phosphorous) are 2-vinylpyridine [2-(2-pyridyl)ethyl] and 4-vinylpyridine [2-(4-pyridyl)ethyl]. An especially preferred vinylpyridine compound herein for all processes and compounds (and its corresponding group when bound to phosphorous) is 2-vinylpyridine[2-(2-pyridyl)ethyl].

In the process for producing 2-(pyridyl)ethyl containing phosphorous compounds, it is preferred if each $R^1$ is independently n-alkyl containing up to about 6 carbon atoms, and especially preferred if $R^1$ is methyl or ethyl. By substituted alkyl or substituted silyl are meant alkyl or silyl groups substituted with groups that do not interfere with the reaction. Suitable groups include, but are not limited to, phenyl, p-chlorophenyl, ether, ester, alkyl, fluoro, and nitrile.

In the process for producing 2-(pyridyl)ethyl containing phosphorous compounds, it is preferred that in the silane, X is chlorine or bromine, and in an especially preferred silane, X is chlorine. A contemplated equivalent for X is iodine. By an oxyanion for X, is meant an anion wherein the negative charge is formally on an oxygen atom. It is also preferred if each $R^2$ is independently an alkyl group or phenyl, more preferred if each $R^2$ is independently a normal alkyl group containing up to 4 carbon atoms or phenyl, and most preferred if $R^2$ is methyl. It is preferred if n is 0 or 2, or 3, and most preferred if n is 3.

Suitable silanes include, but are not limited to, silicon tetrachloride, methyltrichlorosilane, dimethyldichlorosilane, trimethylchlorosilane, trimethylbromosilane, silicon tetrabromide, trimethylsilyl trifluoromethylsulfonate, trimethylsilyl trifluoroacetate, phenylmethyldichlorosilane, phenyltrchlorosilane, triphenylchlorosilane, diphenyldichlorosilane, t-butyltrichlorosilane, n-octadecyltrichlorosilane, and alpha-naphthyl-p-chlorophenyldichlorosilane. Preferred silanes are trimethylchlorosilane, trimethylsilyl trifluoromethylsulfonate, trimethylsilyl trifluoroacetate, trimethylbromosilane, dimethyldichlorosilane, and silicon tetrachloride. Especially preferred silanes are dimethyldichlorosilane, and trimethylchlorosilane.

The silane may be present in catalytically effective amounts, or greater than catalytic amounts, and the product obtained depends upon the amount used. Any catalytically effective amount of silane may be used, and it has been found that about 0.1 (or more) equivalents of the X group per mole of vinylpyridine or starting phosphorous compound is catalytically effective. For one mole of vinylpyridine or phosphorous compound, about 0.1 moles (or more) of trimethylchlorosilane, or 0.025 moles of silicon tetrachloride would be used. Up to about one equivalent of X group the principal desired product obtained has the structure

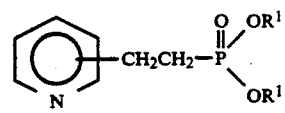

but above about 2.2 equivalents of X, increasing amounts of the structure

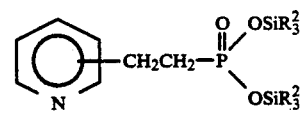

are obtained. At about 3 equivalents of X per mole of vinylpyridine or phosphorous compound, the product consists almost entirely of the latter structure. In the latter case, it will be understood by those skilled in the art, that when there is more than one X group present in the silane, the product may be a complex mixture of oligomers, with some silicon atoms being bound (through oxygen) to more than one phosphorous atom. It is preferred, if more than one equivalent of X group is used, that n in the silane formula be 3. More than 3 equivalents of X group may be used, but it accomplishes nothing advantageous.

When the silane is used, no temperature limitations except those related to starting material and product stability are known, but in order to achieve convenient reaction rates, it is preferred to run the process, if more than about 2.2 equivalents of X per mole of vinylpyridine or phosphorous compound is used, from about 20° C. to about 130° C., preferably about 50° C. to about 130° C., and more preferably about 70° C. to about 120° C., and if less than about 2.2 equivalents of X per mole of vinylpyridine or phosphorous compound are used, from about 0° C. to about 130° C., preferably about 15° C. to about 50° C., and more preferably about 20° C. to about 30° C. The reaction may be run neat or in a solvent, but neat is preferred if less than about one equivalent of X for each mole of vinylpyridine or phosphorous compound is present in the process. Suitable solvents are aprotic solvents that don't react with the silane or other ingredients or products, such as acetonitrile, methylene chloride and toluene. The process may be run in any vessel not affected by the reactants or products, such as glass. Using lower boiling ingredients at higher temperatures may require the use of a pressure vessel, at autogenous pressure.

When the silane is used, is it preferred to exclude water and oxygen, since these may react with the starting materials or products. Small amounts of these may be tolerated, but use up some of the reagents. It is convenient to run the reaction under an inert atmosphere, such as nitrogen or argon. Vigorous agitation is preferred to assure mixing of the reactants. The product may be isolated by distillation, of if high boiling, by evaporation of solvent and byproducts. If oligomers are present because the silane had more than one X group on each silicon atom (n<3), then it may be more convenient to hydrolyze the product to the corresponding phosphonic acid, if that is the desired or useable product. With any of the third compounds present, if the phosphonic acid is the desired product, the reaction mixture may be hydrolyzed in a further step to the acid. The phosphonic acids are also useful as catalysts for increasing the molecular weight of polyamides. Such hydrolyses are known to those skilled in the art, for example E. Maruszewska-Wieczorkowska, supra, which is hereby included by reference.

When any of the third compounds is present, the ratio of vinylpyridine to phosphorous compound is not critical, but an approximately 1:1 molar ratio is desirable, since this results in the most efficient use of the starting materials.

The third compound may be a protic acid whose pKa when measured in water is less than about 6. If water cannot be used to measure the pKa, then the pKa may be measured in dimethylsulfoxide, and compared with similar compounds whose pKa in water is known. Some preferred acids have a pKa of about 1 or less. Preferred protic acids are carboxylic acids and mineral acids. These include, but are not limited to, hydrochloric acid, hydrobromic acid, phosphorous acid, sulfuric acid, formic acid, acetic acid, benzoic acid, trifluoromethanesulfonic acid, trifluoroacetic acid, chloroacetic acid, and isobutyric acid. Preferred acids are hydrochloric acid, hydrobromic acid, formic acid, trifluoroacetic acid, and acetic acid.

When a protic acid is used, the ingredients may be added in any order, but it may be convenient to first combine the protic acid and the vinylpyridine to form the vinylpyridine salt, such as the vinylpyridine hydrochloride. This reaction is exothermic. The salt may be isolated and added as a "pure" compound. Although not critical, it is preferred if the molar ratio of protic acid to vinyl pyridine is about 1. Lower yields will result if this ratio is less than 1, and adding more protic acid is believed not to improve the reaction.

When the protic acid is used, no temperature limitations except those related to starting material and product stability are known, but in order to achieve convenient reaction rates, it is preferred to run the process from about 0° C. to about 130° C., preferably about 15° C. to about 50° C., and more preferably about 20° C. to about 30° C. The reaction may be run neat or in a solvent, but a solvent is preferred. Suitable solvents are aprotic solvents that don't react with the ingredients or products, such as acetonitrile, methylene chloride and toluene. The reaction may be run in any vessel not affected by the reactants or products, such as glass.

When a protic acid is used, is it preferred to exclude water and oxygen, since these may react with the starting materials or products. Small amounts may be tolerated, but use up some of the reagents. It is convenient to run the reaction under an inert atmosphere, such as nitrogen or argon. Vigorous agitation is preferred to assure mixing of the reactants. The product may be isolated by distillation, or if high boiling, by evaporation of solvent and byproducts. A byproduct of the reaction with the protic acid is the compound $R^1Y$. For example if the protic acid is hydrochloric acid and $R^1$ is ethyl, the byproduct will be ethyl chloride. Provision should be made to remove this byproduct, particularly if it is low boiling.

The process may also be carried out in the presence of a third compound which is a Lewis acid. Useful Lewis acids, include, but are not limited to, $TiCl_4$, $AlCl_3$, $AlBr_3$, $SnCl_4$, $BCl_3$, $BBr_3$, and triphenylboron. Preferred Lewis acids are $TiCl_4$, $SnCl_{14}$ and $AlCl_3$. Contemplated equivalents for Z are fluorine and iodine. A catalytically effective amount of the Lewis acid should be used, preferably at least about 0.05 mole of Lewis acid per mole of vinylpyridine, and more preferably about 0.1 to about 0.2 mole of Lewis acid per mole of vinylpyridine.

When the Lewis acid is used, no temperature limitations except those related to starting material and product stability are known, but in order to achieve convenient reaction rates, it is preferred to run the process from about 0° C. to about 130° C., preferably about 15° C. to about 50° C., and more preferably about 20° C. to about 30° C. The reaction may be run neat or in a solvent, but a solvent is preferred. Suitable solvents are polar aprotic solvents that don't react with the ingredients or products, such methylene chloride. The solvent should not coordinate or otherwise substantially react with the Lewis acid. The reaction may be run in any vessel not affected by the reactants or products, such as glass.

When a Lewis acid is used, is it preferred to exclude water and oxygen, since these may react with the starting materials or products. Small amounts of water or oxygen may be tolerated, but use up some of the reagents. It is convenient to run the reaction under an inert atmosphere, such as nitrogen or argon. Vigorous agitation is preferred to assure mixing of the reactants. The product may be isolated by distillation after washing with water and neutralizing any residual inorganic acid, or if high boiling, by evaporation of solvent and byproducts after washing with water and neutralizing.

The products of the above process are useful as catalysts for increasing the molecular weight of polyamides, as described in U.S. Pat. No. 4,912,175, which is incorporated herein.

In another aspect, this invention concerns a compound of the formula

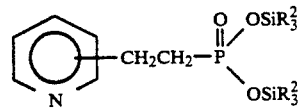

which is made by the above process using a silane wherein n is 3, and more than one mole, and preferably about 3 moles, of silane per mole of vinylpyridine or phosphorous compound is used. It is also preferred if each $R^2$ is independently an alkyl group or phenyl, more preferred if each $R^2$ is a normal alkyl group containing up to 4 carbon atoms or phenyl, and most preferred if $R^2$ is methyl. These preferences also hold for the process in which these compounds are used as catalysts for increasing the molecular weight of polyamides. Similar processes for increasing the molecular weight of polyamides are known to those skilled in the art, for example as described in U.S. Pat. No. 4,912,175, at col. 4, line 51 to col. 5, line 6, and the Examples therein. The general procedures described in U.S. Pat. No. 4,912,175 may be followed with the present compound to increase the molecular weight of a polyamide.

EXAMPLE

Example 1

In a nitrogen-filled drybox, 0.11 g (1.05 mmol) of 2-vinylpyridine and 0.14 g (1.01 mmol) diethylphosphite were combined in 5 mL of $CD_2Cl_2$ and then separated into 5 equal portions. One portion was used as the control; one portion ("A") was treated with 0.010 g (0.09 mmol) $SiMe_3Cl$; one portion ("B") was treated with 0.022 g (0.10 mmol) $SiMe_3O_3SCF_3$; one portion ("C") was treated with 0.015 g (0.10 mmol) $SiMe_3Br$; and one portion ("D") was treated with 0.010 g (0.09 mmol) $SiMe_3Cl$ and 0.010 g (0.10 mmol) $NEt_3$. $^1H$ NMR spectra of the 5 samples were recorded approximately 12 hours after preparation. The control sample had only unreacted starting materials; A had mostly unreacted starting materials but observable amounts (ca. 20%) of diethyl-2-(2-pyridyl)ethylphosphonate ("product") (NMR parameters as in Example 9), together with $SiMe_3$ signals; B and C both had essentially complete conversion of starting materials into compounds having methylene $^1H$ NMR signals analogous to those of product, together with $SiMe_3$ signals; D had no observable amounts of product. The NMR spectrum of sample A was recorded again after ca. 24 additional hours, revealing the formation of additional amounts of product.

Example 2

In a nitrogen-filled drybox, 0.558 g (4.04 mmol) diethylphosphite and 0.425 g (4.04 mmol) 2-vinylpyridine were combined without additional solvent and treated with 0.020 g (0.09 mmol) $SiMe_3O_3SCF_3$. Small samples of this mixture were withdrawn after 5 and 45 minutes, diluted with $CD_2Cl_2$, and used for $^1H$ NMR analysis. No diethyl-2-(2-pyridyl)ethylphosphonate ("product") was observed in either sample. An additional 0.050 g (0.22 mmol) $SiMe_3O_3SCF_3$ was added to the mixture; small samples were withdrawn 15, 60, and 100 minutes after this addition, diluted with $CD_2Cl_2$ and used for $^1H$ NMR analysis. These samples showed progressively increasing conversion of the starting materials to product, and the conversion was essentially complete (>90%) in the 100-minute sample.

It is believed that the lack of observable reaction following the initial addition of 0.020 g $SiMe_3O_3SCF_3$ is the result of traces of moisture ($H_2O$) in the starting materials. Presumably there was enough moisture present to deactivate the initial 0.020 g of $SiMe_3O_3SCF_3$ but not enough to deactivate the additional 0.050 g.

Example 3

In a nitrogen-filled drybox 1.38 g (9.99 mmol) diethylphosphite and 1.05 g (9.99 mmol) 2-vinylpyridine were combined without additional solvent, and treated with 0.22 g (2.02 mmol) $SiMe_3Cl$. Small samples of this mixture were withdrawn after 38, 70, and 115 minutes, diluted with $CD_2Cl_2$, and used for $^1H$ NMR analysis. A fourth sample was taken from the mixture after ca. 48 hours. $^1H$ NMR analysis confirmed the appearance of progressively increasing amounts of diethyl-2-(2-pyridyl)ethylphosphonate ("product") with the conversion of starting materials to product being essentially complete (>90%) after 48 hours.

Example 4

In a nitrogen-filled drybox 1.38 g (9.99 mmol) diethylphosphite and 1.05 g (9.99 mmol) 2-vinylpyridine were combined without additional solvent, treated with 0.20 g (1.84 mmmol) $SiMe_3Cl$, and stirred at room temperature. Small samples were withdrawn after 10, 40, 70, 100, and 130 min, diluted with $CD_2Cl_2$, and kept cold (between 0 and −78 deg C) until analyzed by $^1H$ NMR. A second mixture of diethylphosphite (1.38 g, 9.99 mmol) and 2-vinylpyridine (1.05 g, 9.99 mmol) was treated with 0.50 g (4.60 mmol) $SiMe_3Cl$ and sampled identically. Results of NMR analysis are tabulated below.

In the reaction using 0.50 g $SiMe_3Cl$ it was observed that a precipitate formed very soon after mixing the reagents. In Example 5 it was shown that similar mixtures of 2-vinylpyridine, diethylphosphite, and $SiMe_3Cl$ precipitate a white solid whose $^1H$ NMR spectrum is consistent with that expected for 2-vinylpyridine hydrochloride.

TABLE

| time (min) | ($x^a$, 0.20 g $SiMe_3Cl$) | ($x^a$, 0.50 g $SiMe_3Cl$) |
|---|---|---|
| 10 | 0.15 | 0.20 |
| 40 | 0.47 | 0.62 |
| 70 | 0.62 | 0.75 |
| 100 | 0.71 | 0.82 |
| 130 | 0.76 | 0.87 |

$^a$Fraction of starting materials converted to diethyl 2-(2-pyridyl)ethylphosphonate.

Example 5

In a nitrogen-filled drybox, 1.38 g (9.99 mmol) diethylphosphite, 1.05 g (9.99 mmol) 2-vinylpyridine, and 1.08 g (9.94 mmol) $SiMe_3Cl$ were combined without additional solvent. A white precipitate formed immediately and was isolated (0.15 g). The solution was cooled to −30 deg C whereupon additional amounts of precipitate formed. A small sample of the liquid was withdrawn and analyzed by $^1H$ and $^{31}P$ NMR ($CD_2Cl_2$ solution), revealing signals appropriate for $P(OSiMe_3)(OEt)_2$ and smaller amounts of 2-vinylpyridine and diethyl-2-(2-pyridyl)ethylphosphonate. $^1H$ NMR analysis of the precipitate ($CD_2Cl_2$ solution) revealed signals appropriate for 2-vinylpyridine hydrochloride.

Example 6

In a nitrogen-filled drybox, 0.049 g (0.23 mmol) of crude $P(OSiMe_3)(OEt)_2$ (prepared from trimethylsilyimidazole and diethylphosphite) and 0.030 g (0.29 mmol) 2-vinylpyridine were combined in 2 mL $CD_2Cl_2$, and separated into two portions. One portion was analyzed by $^1H$ NMR with no further additions; the other portion was treated with 0.011 g (0.07 mmol) trifluoromethanesulfonicacid and analyzed by $^1H$ NMR. In each case the analysis was complete within 15 min of mixing. The first portion had no discernable amounts of diethyl-2-(2'-pyridyl)ethylphosphonate ("product") and only unreacted starting reagents were identified; the second portion had essentially complete conversion of phosphate reagents to product and only a small excess of 2-vinylpyridine remained.

In a nitrogen-filled drybox 0.080 g (0.56 mmol) crude 2-vinylpyridine hydrochloride (prepared as in Example 5) and 0.092 g (0.55 mmol) $P(OEt)_3$ were combined in 1 mL $CD_2Cl_2$. $^1H$ NMR analysis (within 24 hrs) revealed essentially complete loss of 2-vinylpyridine and conversion to product.

Example 7

The trimethylsilyl ester of phosphorus acid was prepared separately by combining 0.40 g (4.88 mmol) phosphorus acid, 1.05 g (10.38 mmol) triethylamine, and 1.02 g (9.39mmol) SiMe$_3$Cl in 10 mL tetrahydrofuran, filtering the triethylamine-hydrochloride after 3 days, and evaporating the solution to an oily residue having a $^1$H NMR spectrum appropriate for HP(O)(OSiMe$_3$)$_2$ (SiMe$_3$, 0.3 ppm; HP, 5.7 and 8.0 ppm, in CD$_2$Cl$_2$). A mixture of 0.44 g (1.94 mmol) of this material, 0.21 g (2.00 mmol) 2-vinylpyridine, 0.07 g (0.64 mmol) SiMe$_3$Cl, and ca. 2 mL CH$_2$Cl$_2$ was prepared and filtered, and 0.02 g (0.18 mmol) additional SiMe$_3$Cl was added to the solution. $^1$H NMR analysis after ca. 24 hours revealed little if any coupling product. An additional 0.09 g (0.83 mmol) SiMe$_3$Cl was added to the solution; $^1$H NMR analysis after an additional ca. 24 hours revealed essentially complete conversion to the coupling product, bis(trimethylsilyl)-2-(2-pyridyl)ethylphosphonate.

Example 8

In a nitrogen-filled drybox, 0.44 g (4.18 mmol) of 2-vinylpyridine and 0.56 g (4.05 mmol) of diethylphosphite were combined in 4 mL CD$_2$Cl$_2$. To one mL of this solution was added 0.036 g (0.19 mmol) TiCl$_4$; to another mL of the solution was added 0.013 g (0.10 mmol) AlCl$_3$; to another mL of the solution was added 0.026 g (0.10 mmol) SnCl$_4$. $^1$H NMR spectra, recorded after ca. 24 hr, revealed signals appropriate for diethyl-2-(2-pyridyl)ethylphosphonate in each sample. Approximate conversions were >50% in the sample containing TiCl$_4$ and approx. 30%(+/−10%) in the samples containing AlCl$_3$ and SnCl$_4$.

Example 9

A dry r. b. flask under a positive pressure of nitrogen was loaded with 1500 ml of 2-vinylpyridine (13.9 moles) and 1780 ml of diethylphosphite (13.8 moles). Over the next hour 365 ml of trimethylchlorosilane (2.88 moles) were added slowly dropwise with mechanical stirring, giving a slow exotherm from room temperature to 50° C. Ice bath cooling was first needed about ⅔ into the trimethylchlorosilane addition, and then was applied as needed to maintain the reaction mixture between 35° and 50° C. The exotherm was apparent for nearly 3 hours after completion of the trimethylchlorosilane addition. The reaction mixture was stirred overnight at room temperature.

Volatiles were pulled off the reaction mixture using a vacuum pump protected by a dry ice acetone trap and then two liquid nitrogen traps in series. The dry ice trap collected 130 g of fluid and the first liquid nitrogen trap 300 g. Four product fractions were collected by slow vacuum distillation using a Vigreux column.

| Fraction | Pressure mm | Boiling Pt. | Weight | Oil Bath |
|---|---|---|---|---|
| #1 | 1–0.8 | 146–143° C. | 461.1 g | 194–197° C. |
| #2 | 0.8–0.6 | 143–141° C. | 944.6 g | 191° C. |
| #3 | 0.6–0.5 | 141–136° C. | 997.2 g | 191° C. |
| #4 | 0.5–0.8 | 136–141° C. | 414.3 g | 197° C. |

Note: one must wait several hours for the vacuum to catch hold and not try to force distillation by raising bath temperature. The fractions ranged in color from green to yellow and orange with color deepening on standing. When done on ordinary laboratory scale the product can be nearly white and stable in color. Proton NMR spectra of all four product fractions were as expected except for up to 0.2H of extra (CH$_3$)$_3$Si protons as singlets in the 0 to 0.4 ppm range: 6H 1:2:1 triplet @ 1.3 ppm, 2H multiplet @ 2.2 ppm, 2H multiplet @ 3.1 ppm, 4H multiplet @ 4.1 ppm, and 4 aromatic H @ 7.1, 7.2, 7.6 and 8.5 ppm.

The total yield of diethyl 2-(2-pyridyl)ethylphosphonate was 2817g (84%). Diethyl 2-(2-pyridyl)ethylphosphonate is a severe eye irritant in rabbits, and eye damage is increased by washing with water.

Example 10

A dry r. b. flask was loaded with 108 ml of 2-vinylpyridine (1 mole) and 92 ml of dimethylphosphite (1 mole) under nitrogen. Dropwise addition of 25 ml of dichlorodimethylsilane (0.21 mole) gave exothermic reaction to 86° C. even with ice bath cooling. Once the exotherm subsided the reaction mixture was fitted for vacuum distillation. A possible exotherm was noted around 98° C. The distillation was shut down, the traps cleaned, and distillation recommenced giving 100 g dimethyl 2-(2-pyridyl)ethylphosphonate b$_{0.2}$=131°–146° C. as a yellow fluid. Proton NMR in CDCl$_3$/TMS showed a 2H multiplet at 2.3 ppm, a 2H multiplet at 3.1 ppm, a 6.5 H 1:1 doublet at 3.7 ppm, and 4.5 aromatic H as multiplets between 7.1 and 8.6 ppm.

Example 11

A dry r. b. flask was loaded with 108 ml of 4-vinylpyridine (1 mole) and 129 ml of diethylphosphite (1 mole) under nitrogen. Dropwise addition of 25 ml of trimethylchlorosilane (0.2 mole) gave exothermic reaction to 53° C. with intermittent ice bath cooling. Once the exotherm subsided the reaction mixture was fitted for vacuum distillation. A possible exotherm was noted during distillation with deposition of solids in the lines. The distillation was shut down, the traps cleaned, and distillation recommenced giving 133 g diethyl 2-(4-pyridyl)ethylphosphonate b$_{0.2}$=129°–134° C. as a greenish fluid that turned light yellow on standing. Proton NMR in CDCl$_3$/TMS showed a 6H absorption at 1.3 ppm, 1.9H quintet at 2.1 ppm, 2H multiplet at 2.9 ppm, 4.2H triplet at 4.1 ppm, 2.1H 1:1 doublet at 7.2 ppm, and a 2.1H singlet at 8.5 ppm.

Example 12

A dry flask was loaded with 10.8 ml of 2-vinylpyridine (0.1 mole) and 12.9 ml of diethylphosphite (0.1 mole). Addition of 1 ml of silicon tetrachloride caused the reaction mixture to momentarily gel and exotherm to 136° C. After another 13 minutes the reaction mixture had cooled to 68° C. and another 1.5 ml of silicon tetrachloride were added (0.022 moles total silicon tetrachloride) with stirring causing further thickening and solids formation. Thirty-seven minutes into the run a proton NMR sample was taken. The NMR spectrum taken several hours later found ~92% conversion to diethyl 2-(2-pyridyl)ethylphosphonate in which some of the ethyl groups had been replaced by silicon.

When 0.3 ml of silicon tetrachloride (0.0026 mole) was used the reaction mixture exothermed only to 38° C. and NMR found 35% conversion to diethyl 2-(2-pyridyl)ethylphoshonate after ~5 hours.

Example 13

A dry r. b. flask under a positive pressure of nitrogen was loaded with 54 ml of freshly distilled 2-vinylpyridine (0.5 mole) containing ~0.1 g of hydroquinone and 64 ml of diethylphosphite (0.5 mole). Over the next 18 minutes 60 ml trimethylchlorosilane were added slowly dropwise with magnetic stirring. Occasional ice bath cooling was applied as needed to control temperature between 30° and 50° C. After another 20 minutes an additional 130 ml of trimethylchlorosilane were added dropwise (1.5 moles chlorotrimethylmethylsilane total) and the reaction mixture stirred overnight at room temperature. The reaction mixture, 226 g of a pale yellow solution with a white precipitate, was loaded into a stainless steel bomb and heated for 16 hours at 120° C., developing a maximum pressure of 110 psi. The resulting hazy, red solution was distilled first at atmospheric pressure (to a pot temperature of 100° C., weight 168 g) and then under vacuum, taking a major cut at 0.1 mm from 100° to 133° C., 118.7 g. Assuming this cut to be pure bis(trimethylsilyl) 2-(2-pyridyl)ethylphosphonate, the yield was 72%. Proton NMR in $CDCl_3$/TMS showed a 16.5 H singlet @ 0.9 ppm. a 2.0 H multiplet @ 2.2 ppm, a 2.0 H multiplet @ 3.1 ppm, 2.0 H as two overlapping peaks @ 7.2 ppm, a 1.1 H triplet @ 7.6 ppm, and a 1.1 H doublet 8.7 ppm, in accord with the assumed structure.

A dropping funnel was loaded with 30 g of bis(trimethylsilyl) 2-(2'-pyridyl)ethylphosphonate. About 2 ml were added dropwise to 585 ml of acetone and 15 ml of water with vigorous mechanical stirring, giving a hazy solution. After 12 minutes the original haze developed into solid precipitate and the remaining bis(trimethylsilyl) 2-(2'-pyridyl)ethylphosphonate was added dropwise at ~2 ml/minute over the next 15 minutes. The slurry was stirred another 5 minutes and vacuum filtered. Washing with 100 ml of acetone and drying overnight under vacuum, gave 16.0 g of white solid mp=153°-155° C. The yield of 2-(2-pyridyl)ethylphosphonic acid was 94% starting from bis(trimethylsilyl) 2-(2-pyridyl)ethylphosphonate or 67% starting from 2-vinylpyridine.

Example 14

In a nitrogen-filled drybox, 2.14 g (20 mmol) 2-vinylpyridine and 3.32 g (20 mmol) triethylphosphite were combined in 4.54 g methylene chloride. Separate samples of this solution, each 1.0 g (2.0 mmol 2-vinylpyridine, 2.0 mmol triethylphosphite), were treated with the following acids:

(a) trifluoromethanesulfonic acid, 0.30 g (2.0 mmol);
(b) trifluoroacetic acid, 0.22 g (2.0 mmol);
(c) phosphorus acid, 0.16 g (2.0 mmol);
(d) formic acid, 0.10 g (2.0 mmol);
(e) benzoic acid, 0.25 g (2.0 mmol); and
(f) acetic acid, 0.12 g (2.0 mmol).

Each mixture was stirred for 4 hours at room temperature, then analyzed by $^1H$ NMR ($CD_2Cl_2$ solution). (a), (b) and (c) had essentially complete (>90%) conversion to diethyl-2-(2-pyridyl)ethylphosphonate ("product"); (d) had approximately 57% conversion to product; (e) had approximately 21% conversion to product; and (f) had approximately 23% conversion to product.

Example 15

In a nitrogen-filled drybox, 1.05 g (10 mmol) 2-vinylpyridine and 1.38 g (10 mmol) diethylphosphite were combined. Half of this solution was treated with 0.24 g (1.0 mmol) of triphenylboron and the resulting white suspension was stirred at room temperature. After ca. 16 hours a portion of the suspension was analyzed by $^1H$ NMR ($CD_2Cl_2$ solution), revealing approximately 62% conversion to diethyl 2-(2-pyridyl)ethylphosphonate ("product"). After an additional 24 hours a second portion of the suspension was analyzed similarly, revealing approximately 76% conversion to product.

Although preferred embodiments of the invention have been described hereinabove, it is to be understood that there is no intention to limit the invention to such embodiments, that it is to be understood that modifications and variations may be made thereto, and that the invention is defined by the appended claims.

What is claimed is:

1. A catalytic process for increasing the molecular weight of a polyamide comprising heating a polyamide in the presence of a compound of the formula

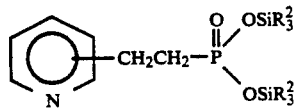

wherein each $R^2$ is independently hydrocarbyl or substituted hydrocarbyl.

2. The process as recited in claim 1 wherein the polyamide is heated in the presence of said compound of the formula

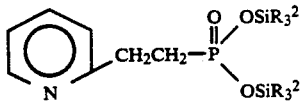

3. The process as recited in claim 1 wherein each $R^2$ is independently an alkyl group or phenyl.

4. The process as recited in claim 3 wherein each $R^2$ is independently a normal alkyl group containing up to four carbon atoms or phenyl.

5. The process as recited in claim 4 wherein said $R^2$ is methyl.

6. The process as recited in claim 2 wherein each $R^2$ is independently a normal alkyl group containing up to four carbon atoms or phenyl.

7. The process as recited in claim 6 wherein said $R^2$ is methyl.

* * * * *